(12) United States Patent
Donley

(10) Patent No.: US 8,371,438 B2
(45) Date of Patent: Feb. 12, 2013

(54) DISPENSING CONTACT LENS CLEANING LIQUID

(76) Inventor: Keith K. Donley, Port Aransas, TX (US)

( * ) Notice: Subject to any disclaimer, the term of this patent is extended or adjusted under 35 U.S.C. 154(b) by 0 days.

(21) Appl. No.: 13/507,113

(22) Filed: Jun. 5, 2012

(65) Prior Publication Data

US 2012/0251405 A1 Oct. 4, 2012

Related U.S. Application Data

(60) Continuation of application No. 13/135,923, filed on Jul. 19, 2011, now abandoned, which is a division of application No. 11/825,783, filed on Jul. 9, 2007, now Pat. No. 7,998,405.

(51) Int. Cl.
B65D 81/24 (2006.01)
(52) U.S. Cl. .............. 206/5.1; 206/216; 422/28; 215/18
(58) Field of Classification Search .................... 422/28, 422/37, 292; 206/5.1, 223, 216; 215/18
See application file for complete search history.

(56) References Cited

U.S. PATENT DOCUMENTS

| | | | |
|---|---|---|---|
| 2,565,872 | A | 8/1951 | Melsheimer |
| 3,402,747 | A | 9/1968 | Tissot-Dupont |
| 3,473,886 | A | 10/1969 | Leeds |
| 3,912,451 | A | 10/1975 | Gaglia |
| 4,011,941 | A | 3/1977 | Parsons |
| 4,169,124 | A | 9/1979 | Forstrom et al. |
| 4,207,287 | A | 6/1980 | Lindquist |
| 4,784,167 | A | 11/1988 | Thomas |
| 4,852,592 | A | 8/1989 | DiGangi et al. |
| 4,905,819 | A | 3/1990 | Clements |
| 5,089,240 | A | 2/1992 | Perlaky |
| 5,127,517 | A | 7/1992 | Clements |
| 5,270,002 | A | 12/1993 | Neff |
| 5,388,686 | A | 2/1995 | Kanner |
| 5,897,833 | A | 4/1999 | Hunt et al. |
| 6,228,333 | B1 | 5/2001 | Mueller-Lierheim |

*Primary Examiner* — Sean E Conley
(74) *Attorney, Agent, or Firm* — G. Turner Moller

(57) ABSTRACT

The eyes of a contact lens wearer are protected from the effects of a liquid disinfecting solution by providing a contact lens container having a catalyst therein and a container of the disinfecting solution of unusual design. The openings of the contact lens container and the solution container are configured so only the contact lens container is able to receive solution from the solution container. This prevents the user from directly removing disinfecting solution from the solution container and thereby prevents the user from directly applying the disinfecting solution to the eye.

19 Claims, 3 Drawing Sheets

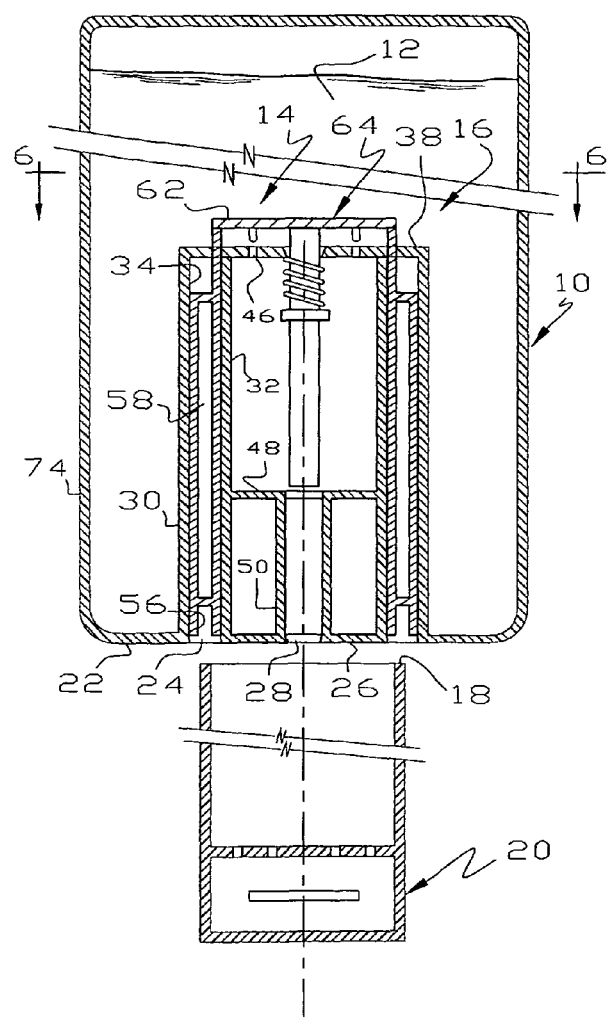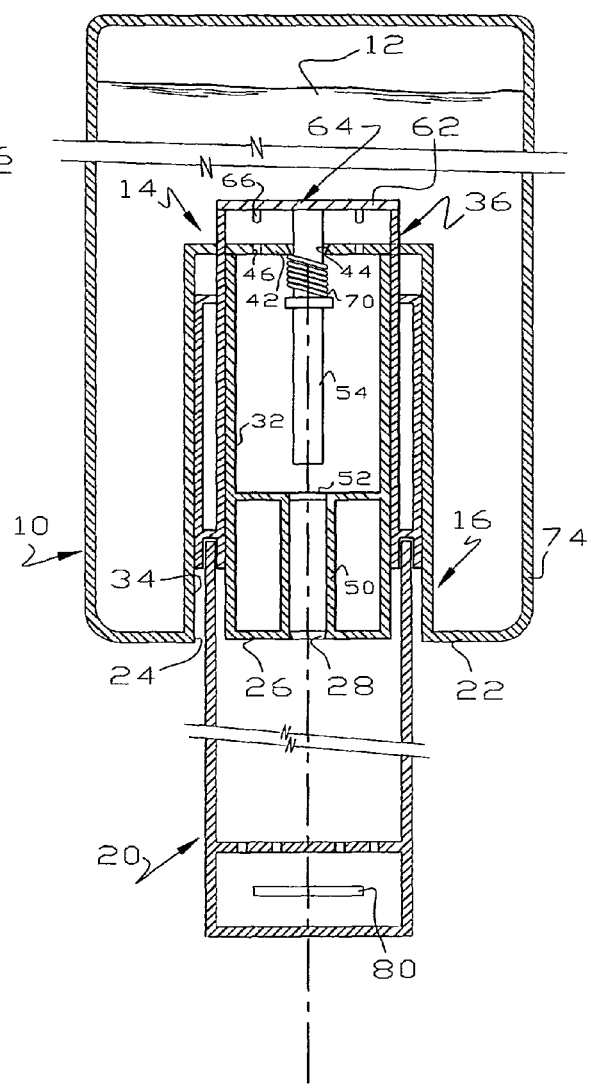

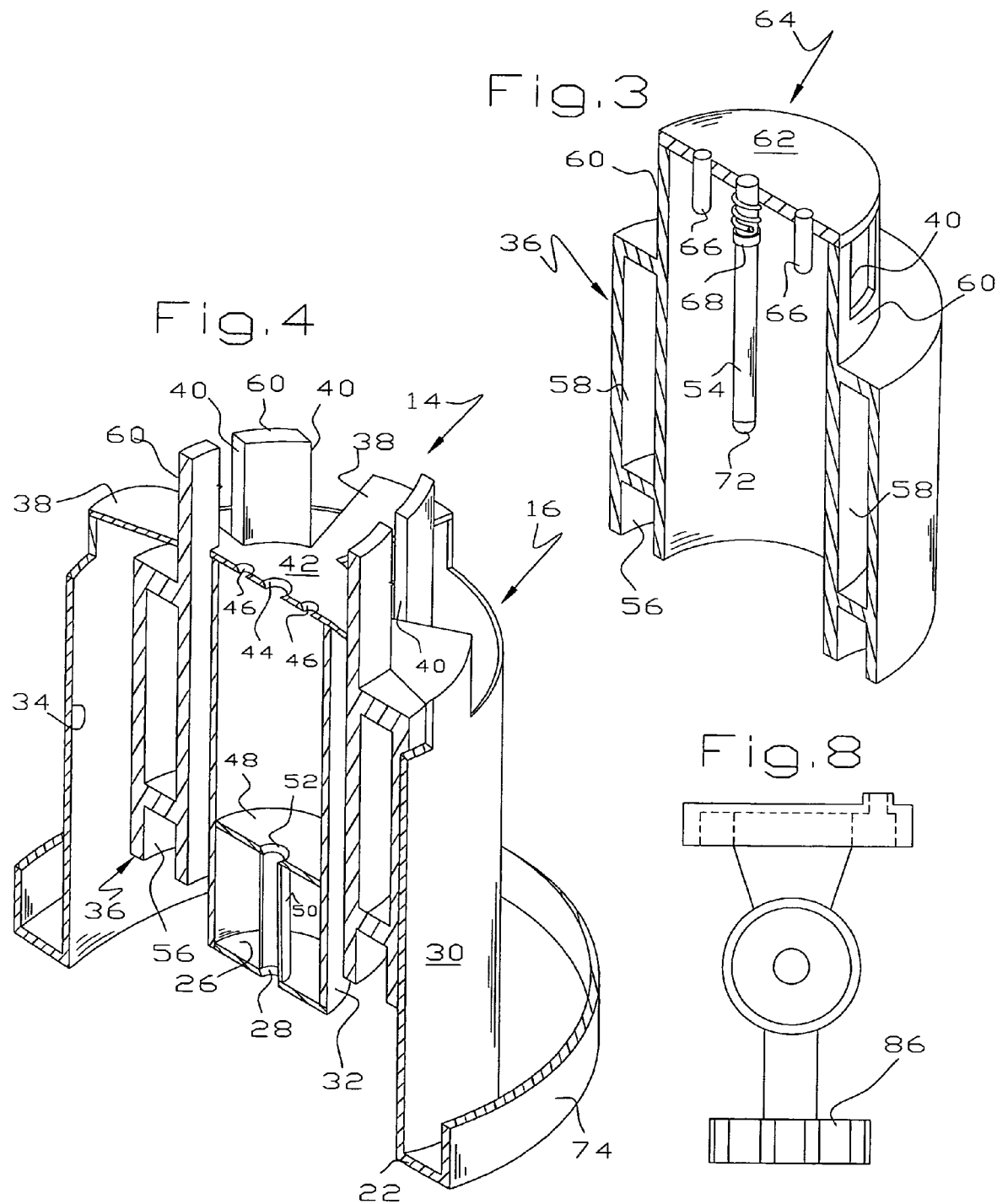

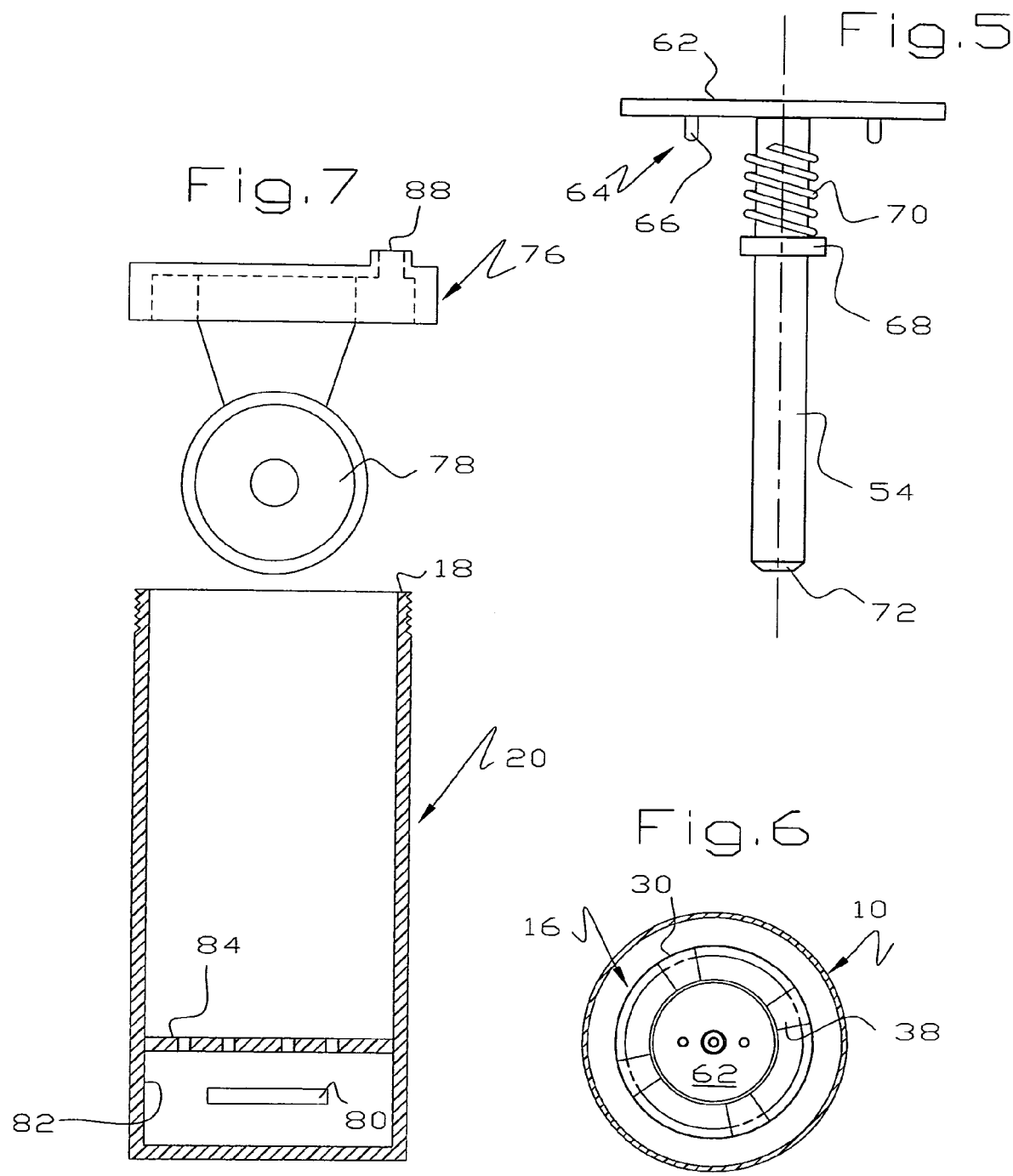

DISPENSING CONTACT LENS CLEANING LIQUID

This application is a continuation of U.S. patent application Ser. No. 13/135,923, filed Jul. 19, 2011, now abandoned which is a division of U.S. patent application Ser. No. 11/825,783, filed Jul. 9, 2007, now U.S. Pat. No. 7,998,405.

This application is based on Provisional Application Ser. No. 60/819,092, filed Jul. 7, 2006, priority of which is hereby claimed.

This invention relates to an apparatus for and a method of protecting the eyes of the wearers of contact lenses from irritating liquid lens cleaning solutions and more particularly to a fool proof method and apparatus of transferring the irritating lens cleaning solution to a contact lens container.

BACKGROUND OF THE INVENTION

Contact lenses are commonly worn by many people. Currently, it is estimated that 125 million people world wide enjoy the comfort, convenience and cosmetic appearance that contact lenses provide. In order to receive these benefits, proper maintenance of contact lenses is necessary. Although some contact lenses are designed to be worn for a short period and then thrown away, it is more common for users to periodically disinfect contact lenses to reduce or eliminate harmful microorganisms such as fungi and bacteria. While disinfecting contact lenses, they are also cleaned of protein, lipid deposits and particulates that accumulate on the lenses.

To date, the single most effective method of disinfecting contact lenses is by immersing the lenses in an aqueous hydrogen peroxide solution. As suggested in U.S. Pat. No. 3,912,451, disinfecting with hydrogen peroxide is conveniently done in the presence of a catalyst so that the hydrogen peroxide is decomposed to produce water and gaseous oxygen. Hydrogen peroxide is a known effective disinfectant and, with one requirement recognized in the prior art, is eminently suitable for disinfecting contact lenses and is, in fact, the preferred disinfectant. The known requirement is that the hydrogen peroxide must be neutralized before the contact lens is reinserted into the user's eye. Otherwise, the hydrogen peroxide causes significant pain and discomfort and may potentially cause eye injury. The degree of pain and discomfort varies, given differences in individual sensitivity and variations in the strength of the hydrogen peroxide solution when exposed.

By placing the contact lens in a container having a catalyst therein, the hydrogen peroxide decomposes in a relatively predictable manner. Thus, placing the contact lens in the container, conveniently before retiring for the night, produces a neutralized solution by the next morning. This process, accelerated by the catalyst, reduces the hydrogen peroxide from a 3% or so solution to a 10-30 parts per million solution by morning. So far as is known, almost all users can tolerate a 10-30 parts per million solution and thus safely insert the contact lenses in their eyes.

It is known to provide containers for several different types of liquid with dispensing spouts so they dispense into their intended receiver. For example, water is provided in containers with valved spouts actuated by pressing on the top of lead-acid automotive batteries so the water is delivered directly into openings in the top of the battery.

Disclosures relative to this invention are found in U.S. Pat. Nos. 3,402,747; 3,473,886; 3,912,451; 4,011,941; 4,784,167; 4,905,819; 5,089,240; 5,127,517; 5,270,002 and 6,228,333.

SUMMARY OF THE INVENTION

In this invention, the disinfecting solution container and the contact lens container are designed so the solution container can only dispense into a contact lens container designed to mate with the solution container. This means the user cannot retrieve disinfecting solution directly from the container—it has to go into the lens container. In one way or another, the lens container provides a catalyst therein so the hydrogen peroxide decomposes at a predetermined rate, dependent mainly on hydrogen peroxide concentration and temperature. In some commercially available contact lens containers, the catalyst is located on a cap-stem assembly providing compartments for the contact lenses so the lenses and catalyst are mounted on the same support, meaning that when the lenses are placed in the container, the catalyst is also placed in the container.

The solution container is preferably non-refillable so the user cannot discharge hydrogen peroxide from a refilling container into the solution container. It is recognized that the design of the solution container and the contact lens container may vary widely.

The solution container includes a dispensing or pour opening having a valve controlling flow through the opening. The solution container is non-refillable, meaning that any fill ports are sealed and no removable caps provide access to the interior of the solution container. The valve operator is inaccessible to a human finger. By making the solution container and the lens container with a unique mating coupling, the solution container can only be mated with and dispense into the lens container.

The valve is closed when the container is upside down, i.e. in a dispensing or pouring position, either in response to the weight of liquid in the container, in response to spring pressure and/or by other techniques. The lens container, in a more-or-less upright position, mates with the solution container, in a pouring position, and includes an element to push the valve to an open position allowing discharge of liquid, preferably by gravity, from the solution container into the lens container. The user controls the amount of solution passing into the lens container simply by raising the solution container and/or lowering the lens container and thereby allowing the valve to close.

There is accordingly provided an improved method and apparatus for transferring an irritating disinfectant into a contact lens container in order to disinfect and clean contact lenses and largely preventing the user from accidentally getting the irritating solution into an eye.

It is an object of this invention to provide an improved apparatus for and method of using a contact lens disinfecting solution that is irritating to the human eye.

A further object of this invention is to provide an improved apparatus for and method of transferring a disinfecting solution from a storage container to a contact lens container.

These and other objects and advantages of this invention will become more apparent as this description proceeds, reference being made to the accompanying drawings and appended claims.

BRIEF DESCRIPTION OF THE DRAWINGS

FIG. 1 is a cross-sectional view of a solution container and a spaced lens container, the solution container being illustrated with the valve slightly raised from its normally closed position;

FIG. 2 is a cross-sectional view of the solution container and lens container when mated and transferring disinfecting solution;

FIG. 3 is an enlarged isometric cross-sectional view of the valve inside the solution container;

FIG. 4 is an enlarged isometric view of the valve of FIG. 3 in position inside a valve housing provided by the solution container;

FIG. 5 is a side view of the valve element inside the solution container;

FIG. 6 is an enlarged cross-sectional view of the solution container of FIG. 1, taken substantially along line 6-6 thereof as viewed in the direction indicated by the arrows;

FIG. 7 is an exploded, partly cross-sectional view of one embodiment of a lens container; and FIG. 8 is a side view of another embodiment of a lid assembly for a lens container.

DETAILED DESCRIPTION OF THE INVENTION

Despite the effectiveness of hydrogen peroxide, its use for disinfecting contact lenses has remained limited because of the potential for injury or pain to the user's eyes. There are several potential reasons why hydrogen peroxide may inadvertently get into the eye of a user: (1) the ineffectiveness of the catalyst to decompose hydrogen peroxide, (2) the impatience or inability of the user to leave the contact lenses in the catalyst container long enough for the catalyst to do its work, (3) the lens container does not have a catalyst to promote decomposition of the hydrogen peroxide, (4) the user wets the contact lens directly with a hydrogen peroxide solution and then, more or less immediately, places the lens in the eye and (5) the user places hydrogen peroxide directly into the eye. It will accordingly be seen that there is another requirement promoting widespread use of hydrogen peroxide for contact lens disinfecting, i.e. preventing the user from more-or-less directly putting disinfectant strength hydrogen peroxide in the eye or onto the lens.

The three most common misuses of a hydrogen peroxide disinfecting scenario are:

1. Following the neutralization process, the user rinses the contacts with full strength hydrogen peroxide from the solution bottle and then inserts the contact lenses in the eye. This is a common habit of users of non-hydrogen peroxide disinfectants, such as the so called "multipurpose" solutions that are currently commercially available. This is routinely done by users who want to re-wet their lenses before inserting them into the eye.

2. The user squirts full strength hydrogen peroxide directly into the eye from a solution container. During normal wear, contact lenses occasionally become dry and uncomfortable. Often, a contact lens wearer using a non-hydrogen peroxide or "multipurpose" solution will squirt the solution into the eye to overcome dryness and improve comfort. If this is done with a hydrogen peroxide disinfectant, a corneal burn may occur.

3. The contact lens wearer uses a contact lens storage case provided with a "multipurpose" cleaning solution instead of a catalyst included storage case intended specifically for use with hydrogen peroxide. The "multipurpose" lens cases do not include a catalyst and consequently the hydrogen peroxide is not neutralized. Again, pain and potential injury follow.

Because of the potential for patient discomfort or injury, the majority of optometrists and ophthalmologists encourage the use of so-called multipurpose solutions to clean contact lenses and thereby disinfect them of fungi and bacteria. However, much attention has been focused recently on the problems of some non-hydrogen peroxide disinfectants. At least one type of multipurpose solution is thought to allow the propagation of eye damaging parasites such as acanthamoeba keratitis. In other situations, there have been reported cases of blindness and/or the market withdrawal of some commercial "multipurpose" solutions. This has led to an increased use of hydrogen peroxide solutions which has naturally led to increased frequency of pain, discomfort and injury to people misusing hydrogen peroxide disinfectants.

Since the start of using hydrogen peroxide as a contact lens disinfectant, there has been no successful technique for eliminating the above three common misuses. It these misuses were minimized or eliminated, there would be a dramatic drop in pain and injury from hydrogen peroxide disinfectant. This will naturally lead to increased use of hydrogen peroxide disinfectants thereby substantially improving eye health of contact lens wearers. This is particularly true of many different types of users who are particularly prone to eye problems from allergies, eye-sensitive users, atypical contact lens wearers and those who generate significant amounts of heavy protein or lipid deposits on their contact lenses. In addition, if the problems of conventional hydrogen peroxide disinfectants can be overcome, eye care professionals will more likely recommend use of hydrogen peroxide thereby promoting greater eye health.

Referring to FIGS. 1-6, a solution container 10 is at least partially filled with a liquid contact lens disinfectant 12 that is irritating to the human eye. Although the disinfectant 12 may be of any suitable type, hydrogen peroxide is much preferred and is, in fact, an ideal disinfectant for contact lenses. Currently, hydrogen peroxide is believed to be the most effective disinfectant for contact lenses and its limited acceptance, to date, is due to the misuse potential of hydrogen peroxide rather than a function of its effectiveness as a disinfectant. For use in contact lenses, hydrogen peroxide is provided in an aqueous solution, typically saline, as disclosed in some detail in U.S. Pat. No. 3,912,451, to which reference is made for a more complete description of the preparation of a suitable hydrogen peroxide solution. The aqueous hydrogen peroxide may also contain other additives, such as surfactants, special cleansers for lipids or proteins, and the like.

An important feature of this invention is that the solution container 10 is non-refillable, meaning that it is sealed against disassembly and is free of closures which can be opened, such as by screw threads, friction fits or the like. The reason for making the container 10 non-refillable is that much of the protection afforded by this invention is compromised by making the container 10 openable and/or resealable. For example, if the container 10 could be opened, a user might be tempted to open the container 10 or the container used to refill the container 10 and put the disinfectant solution directly on the contact lens or into his eye.

The container 10 also includes a normally closed valve 14 including a valve housing 16 of unusual design. The valve 14 is preferably arranged so that it can substantially only be opened by the open mouth 18 of a lens container 20, meaning it is virtually impossible to dispense the contents other than into the lens container 20. By virtually impossible, it is meant that the valve 14 cannot be operated by a human finger of any size, child or adult, or by a human finger nail larger than 1/64th inch thick or shorter than 1/4 inch long. The latter requirement may be accommodated in a number of different ways, e.g. by making the valve 14 so it will not open when pushed only on one side as illustrated in FIGS. 1 and 2 or by other techniques.

Although it is preferred to design the valve 14 and valve housing 16 so the lens container 20 does not have to be modified, it is, of course, equally within the scope of this invention to provide a lens container 20 which is modified in some manner to manipulate a specifically designed valve 14 so they are a unique, mating coupling which will only transfer liquid disinfectant from the container 10 to the container 20.

The container 10 includes a bottom wall 22 having valve operating opening 24 which is preferably in the form of a closed arcuate slot such as a circle. It will be noted that the valve operating opening 24 is sufficiently small that a human finger cannot pass through it to manipulate the valve 14. The valve operating opening 24 will be seen to be sized to be slightly larger than the open mouth of the lens container 20, as explained more fully hereinafter. The bottom wall 22 includes a section 26 inside the valve operating opening 24 which provides a disinfectant dispensing opening 28, all as more fully apparent hereinafter.

The valve housing 16 is mounted on the bottom wall 22 and includes an outer cylindrical wall 30 and an inner cylindrical wall 32 providing an annulus 34 for receiving an annular valve operator 36. The inner cylindrical wall 32 is supported from the container 10 in any suitable manner, as by the provisions of struts 38 extending from the outer wall 30 through slots 40 in the valve operator 36 as shown best in FIG. 4. The struts 38 not only support the inner wall 32 but also register the valve operator 36 to prevent it from rotating and ultimately misaligning the sealing elements of the valve 14.

The bottom of the inner wall 32 is sealed against the bottom wall section 26 and includes a top wall 42 having a central opening and a series of valve openings 46 as more fully explained hereinafter. The valve housing 16 also includes an interior wall 48 preferably parallel to and spaced from the bottom wall section 26 and a tube 50 provides communication between the inside of the wall 32 and the dispensing opening 28. The interior wall 48 provides a valved opening 52 allowing and preventing flow of disinfectant out of the container 10. The dispensing opening 28 is preferably too small to accommodate a human finger so the valve stem 54 cannot be intentionally unseated by extending a human finger through the opening 28. In addition, one purpose of the double walls 26, 48 is to recess a valve stem 54 so it cannot be reached by inserting a small object, such as a pencil, through the opening 28 to unseat the valve stem 54.

The annular valve operator 36 provides an annular lower slot 56 sized to closely receive the open mouth 18 of the lens container 20, a central section 58 that is box shaped in cross-section and an upper annular extension or skirt 60 that pushes on a plate 62 comprising part of a valve element 64. The skirt 60 includes the slots 40 which allow the valve operator 36 to move upwardly past the struts 38 that support the inner wall 32 as shown best in FIGS. 3 and 4. It will accordingly be seen that when the valve operator 36 is raised, the skirt 60 is raised to push on the underside of the plate 62 thereby raising the valve element 64 and opening the container 10 so liquid disinfectant flows into the lens container 20. The width and depth of the slot 56 is such that a human finger cannot enter the slot 56 and raise the valve operator 36 a sufficient distance to open the valve element 64. In the alternative, or in addition, the annular section 74 of the container 10 may be lengthened to extend below the lower end of the valve operator 36 to further isolate the valve operator 36 from intentional operation by other than the lens container 20.

The valve element 64 comprises the plate 62, one or more sealing elements 66 sealing the valve openings 46, the stem 54 having a shoulder 68 thereon and a compression spring 70 acting between the shoulder 68 and the top wall 42 of the valve housing 16. It will be seen that the spring 70 pushes the end 72 of the stem 54 into sealing engagement with the valved opening 52 and to push the plate 62 so the sealing elements 66 close the valve openings 46. Thus, the valve 14 acts to seal against downward flow of liquid disinfectant by the valve elements 46, 66 and by the valve elements 52, 72. It will accordingly be apparent that the valve 14 may be simplified by eliminating one set of the valve elements. It will also be evident that the plate 62 of the valve element 64 may be bonded to, or separate from, the skirt 60 of the valve operator 36.

The valve operator 36 is preferably made to close enough tolerances, relative to the diameter of the inner cylindrical wall 32 on which it slides, that the operator 36 is not easily operated from only one edge as may be attempted by someone pushing on it with a small object. Pushing on one edge of the operator 36 tends to tilt the operator 36, which is resisted by its close tolerance with the cylindrical wall 32, thereby effectively jamming the operator 36 and promoting operation of the valve operator 36 only by a circular object of the correct size, i.e. the open mouth 18 of the lens container 20. The close tolerance between the outside of the valve operator 36 and the inside of the outer wall 30 also prevents or minimizes leakage of disinfectant during dispensing.

It will be immediately apparent that many different valve designs are capable of discharging an aqueous hydrogen peroxide disinfectant exclusively into a lens container 20.

By stating that the transfer is only, exclusively or substantially exclusively between the solution container 10 and the lens container 20, it is meant that transfer is substantially capable only from the solution container 10 in response to mating with a element that is essentially identical to the open mouth 18 of the lens container 20.

The lens container 20 may be of any suitable design and is preferably conventional comprising an open mouth 18 for interdigitating with the valve operator 36 and a lid assembly 76 which connects with the container mouth 18 in any suitable fashion, as by the provision of threads or a friction fit. The lid assembly 76 includes one or more contact lens holders 78 supporting contact lenses inside the container 20. A catalyst body 80 is provided, either in a separate compartment 82 under a perforated divider 84 as shown in FIG. 7 or as an attachment 86 on the end of the lens holders 78 as shown in FIG. 8. In any event, the container 20 includes a catalyst therein when contact lenses are immersed in the liquid disinfectant. Although the catalyst may be of any suitable type, platinum is preferred because it is commonly used in commercially available lens containers as discussed in U.S. Pat. No. 3,912,451. The lid assembly 76 includes a conventional check valved opening 88 to allow the release of oxygen generated during the decomposition of hydrogen peroxide.

Operation of the solution container 10 and the lens container 20 should now be apparent. When the wearer is ready to remove contact lenses for cleaning, the lid assembly 76 is removed and the contact lenses placed in the holders 78. The solution container 10 is placed over the open lens container 20 and aligned so the open mouth 18 enters the slot 56 of the valve operator 36. The solution container 10 is then lowered so the valve operator 36 moves upward relative to the inner wall 32 thereby raising the plate 62 and shifting the valve element 64 to an open position. When the lens container 20 contains sufficient liquid disinfectant, the solution container 10 is raised allowing the spring 70 to push the valve stem 54 relatively downward to close the valve elements 46, 66 and 52, 72 and thereby stop flow of the liquid disinfectant. The lens container 20 is closed with the lid assembly 76 so the contact lenses and any catalyst on the lid assembly 76 are immersed in the liquid disinfectant. The contact lenses are left in the container 20 for a time period sufficient to allow the catalyst to decompose the liquid disinfectant thereby lowering its concentration to a level that is easily tolerated by the human eye.

It will accordingly be seen that this invention eliminates many of the potential misuses of irritating liquid disinfectants.

Although this invention has been disclosed and described in its preferred forms with a certain degree of particularity, it is understood that the present disclosure of the preferred forms is only by way of example and that numerous changes in the details of operation may be resorted to without departing from the spirit and scope of the invention as hereinafter claimed.

I claim:

1. In combination, a liquid hydrogen peroxide solution container and a contact lens container,
    the liquid solution container comprising a dispensing opening having therein a valve movable between a normally closed position and an open position, a valve operating mechanism and a valve operating opening adapted to receive an element of a lens container and thereby manipulate the valve operating mechanism to move the valve to the open position, the operating opening having an inner wall and an outer wall providing an annular slot therebetween of a size inaccessible by a human finger; and
    the contact lens container comprising an open mouth having an inner passage and an outer dimension having a wall thickness therebetween providing an annular lip received in the annular slot of the solution container pushing the valve upwardly into the open position so liquid hydrogen peroxide can flow by gravity through the dispensing opening into the lens container; and
    a catalyst in the lens container accelerating the decomposition of hydrogen peroxide.

2. The combination of claim 1 wherein the valve operating opening is independent of the dispensing opening.

3. The combination of claim 1 wherein the solution container is non-refillable.

4. The combination of claim 1 further comprising a spring biasing the valve toward the closed position.

5. The combination of claim 1 wherein the annular slot is circular and the lens container mouth is circular.

6. The combination of claim 1 wherein the lens container includes a lid having a contact lens support thereon for supporting contact lenses in the hydrogen peroxide solution.

7. The combination of claim 6 wherein the lens support includes a catalyst support.

8. The combination of claim 1 wherein the valve operating opening is spaced from the dispensing opening.

9. The combination of claim 1 wherein the valve operating opening surrounds the dispensing opening.

10. The combination of claim 1 wherein the open mouth of the contact lens container is free of a valve.

11. A liquid hydrogen peroxide solution dispenser comprising
    a container having
        a dispensing opening having therein a valve movable between a normally closed position and an open position,
        an inner wall and an outer wall providing an annular gap therebetween providing a valve operating opening independent of the dispensing opening and of a size inaccessible by a human finger, and
        a valve operating mechanism adapted to move the valve to the open position in response to inserting an open mouth of a lens container into the valve operating opening.

12. The dispenser of claim 11 wherein the annular gap is circular.

13. The dispenser of claim 11 wherein the annular gap is spaced from the dispensing opening.

14. The dispenser of claim 11 wherein the annular gap surrounds the dispensing opening.

15. A liquid hydrogen peroxide solution dispenser comprising
    a container having a dispensing opening including a valve movable between an open and a closed position,
    concentric inner and outer walls providing an annular gap therebetween providing a valve operating opening, and
    valve operating means for moving the valve to the open position in response to inserting a rim of an open mouth of a lens container into the valve operating opening, the valve operating opening being spaced from the dispensing opening and of a size inaccessible by a human finger.

16. The dispenser of claim 15 wherein the valve operating opening surrounds the dispensing opening.

17. The dispenser of claim 15 wherein the valve operating opening is independent of the dispensing opening.

18. In combination, a liquid hydrogen peroxide solution container and a contact lens container,
    the liquid solution container comprising a dispensing opening having therein a valve movable between a normally closed position and an open position, a valve operating mechanism and a valve operating opening adapted to receive an element of a lens container and thereby manipulate the valve operating mechanism to move the valve to the open position, the operating opening being of a size inaccessible by a human finger;
    the contact lens container comprising an open mouth free of valve means therein and having a component inserted into the operating opening, manipulating the valve operating mechanism so liquid hydrogen peroxide can flow by gravity through the dispensing opening into the lens container; and
    a catalyst in the lens container accelerating the decomposition of hydrogen peroxide.

19. The combination of claim 18 wherein the valve operating opening is spaced from the dispensing opening.

* * * * *